US006733470B1

(12) United States Patent
DeGeorge et al.

(10) Patent No.: US 6,733,470 B1
(45) Date of Patent: May 11, 2004

(54) TRACTION FORCE APPLYING APPARATUS AND METHOD OF USING THE SAME

(75) Inventors: Dwight J. DeGeorge, Lynnfield, MA (US); Sanghak O. Harrison, Evanston, WY (US); Leonard A. Siskin, Randolph, NJ (US)

(73) Assignee: Promote Chiropractic, Inc, Saugus, MA (US)

( * ) Notice: Subject to any disclaimer, the term of this patent is extended or adjusted under 35 U.S.C. 154(b) by 0 days.

(21) Appl. No.: 09/690,939

(22) Filed: Oct. 17, 2000

(51) Int. Cl.[7] .................................................. A61F 5/00

(52) U.S. Cl. ......................................... 602/32; 606/241

(58) Field of Search .............................. 602/32, 33, 34, 602/35, 36, 38, 39, 40; 606/241; 482/130–133; 601/24, 26, 33

(56) References Cited

U.S. PATENT DOCUMENTS 2,373,456 A * 4/1945 Chapman ..................... 602/34
2,714,885 A * 8/1955 Uhland ........................ 602/32
2,875,753 A * 3/1959 Sumonetti .................... 602/34
3,003,498 A * 10/1961 Hotas .......................... 602/32
4,951,654 A 8/1990 Gambale et al. ............ 606/242
5,129,881 A * 7/1992 Pope ........................... 602/32
5,409,452 A * 4/1995 Aversano .................... 482/142
5,575,765 A * 11/1996 Foster .......................... 602/32
5,577,984 A * 11/1996 Bare, II ...................... 482/123

* cited by examiner

*Primary Examiner*—Danton D. DeMille
*Assistant Examiner*—Quang D Thanh
(74) *Attorney, Agent, or Firm*—Henry E. Naylor

(57) ABSTRACT

A traction force applying apparatus includes a frame that has a first support bar, a second support bar and a third support bar. The second support bar is fixedly connected to the first support bar adjacent to a first end thereof. The third support bar is fixedly connected to the first support bar near a second end thereof. A first set of plurality of hooks are fixedly attached to a first side of the first support bar. A second set of plurality of hooks are fixedly attached to a first side of the second support bar. A one-way tensioning cleat is fixedly connected to the first support bar. The apparatus also includes a rope that has a first end and a second end. The first end of the rope is selectively connectable to one of the plurality of hooks in the first set and the second set. The rope extends through the cleat to place a desired tension on the rope between the cleat and the first end of the rope. The traction force applying apparatus can be used alone or in combination with a traction table.

25 Claims, 16 Drawing Sheets

TRACTION FORCE APPLYING APPARATUS AND METHOD OF USING THE SAME

BACKGROUND OF THE INVENTION

1. Field of the Invention

The present invention relates to a traction force applying apparatus and method of using the same. More specifically, the present invention relates to an apparatus that applies force to the body to restore the spine to its natural biomechanical configuration.

2. Discussion of the Related Art

To correct for back and/or neck problems, chiropractors and other practitioners sometimes use a traction table so that a person's spinal curve can be directed towards the position and/or shape that nature intended (i.e., the natural biomechanical position and/or shape to support the human body in the upright position).

One such traction table is disclosed in U.S. Pat. No. 4,951,654 to Gambale, et al. Gambale's traction table has a support surface to support the buttocks of a person and an inclined support surface to support the back. The head of the patient extends beyond the upper portion of the inclined support surface so that the head can be inclined backwardly with respect to the spine. A forehead sling is mounted on an upper portion of the traction table to pull the forehead of the person downwardly, thereby applying a compressive force at an acute angle with respect to the upper spine of the patient. The patient is then intended to remain in this position for an extended period of time (e.g., anywhere from 10 minutes, if the patient can tolerate staying in this position for that long, up to 30 minutes). At approximately 25–30 minutes, the body tissues reach an optimal deformation, and, thereafter, the rate of tissue deformation diminishes to the point where it is no longer worth keeping the patient in the apparatus.

This type of traction table has proven to be successful in correcting back or neck problems in some patients. However, the present inventors have discovered that the traction table, even with the use of cushions inserted under the spine, which only apply a passive reactive force to the patient, when used alone, or in conjunction with extension and/or compression traction, fails to provide adequate force to the body to restore the spine to its natural biomechanical configuration.

Accordingly, it is an object of the present invention to provide a traction force applying apparatus that applies an adjustable force to a patient's body at an adjustable angle, according to the patient's individual needs, to sufficiently restore the patient's spine, including the cervical, thoracic and lumbar regions thereof, to approximately its natural biomechanical configuration.

SUMMARY OF THE INVENTION

In accordance with a currently preferred exemplary embodiment of the present invention, this and other objects of the present invention are achieved with a traction force applying apparatus that includes a frame that has a first support bar, a second support bar and a third support bar. The second force applying bar is fixedly connected to the first support bar near a first end thereof. The third support bar is fixedly connected to the first support bar near a second end thereof. A first set of plurality of hooks are fixedly attached to a first side of the first support bar. A second set of plurality of hooks are fixedly attached to a first side of the second support bar. A one-way tensioning cleat is fixedly connected to the first support bar. The apparatus also includes a rope that has a first end and a second end. The first end of the rope is selectively connectable to one of the plurality of hooks in the first set and the second set. The rope extends through the cleat to place a desired tension on the rope between the cleat and the first end of the rope.

In accordance with another currently preferred exemplary embodiment of the present invention, this and other objects of the present invention are achieved with a traction force applying apparatus that includes a base and a U-shaped frame. The U-shaped frame has a pair of legs and a cross-bar. A distal end of each of the legs is selectively fixedly connected to the base. A winch is fixedly connected to the cross-bar. A rope has a first end and a second end. The first end of the rope is connected to the winch. The second end of the rope is connected to a second cross-bar. A strap has a first end and a second end. The strap first end is connected to a first end of the second cross-bar. The strap second end is connected to a second end of the second cross-bar.

BRIEF DESCRIPTION OF THE DRAWING FIGURES

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein.

DETAILED DESCRIPTION OF THE PREFERRED EMBODIMENT

Figure 1:
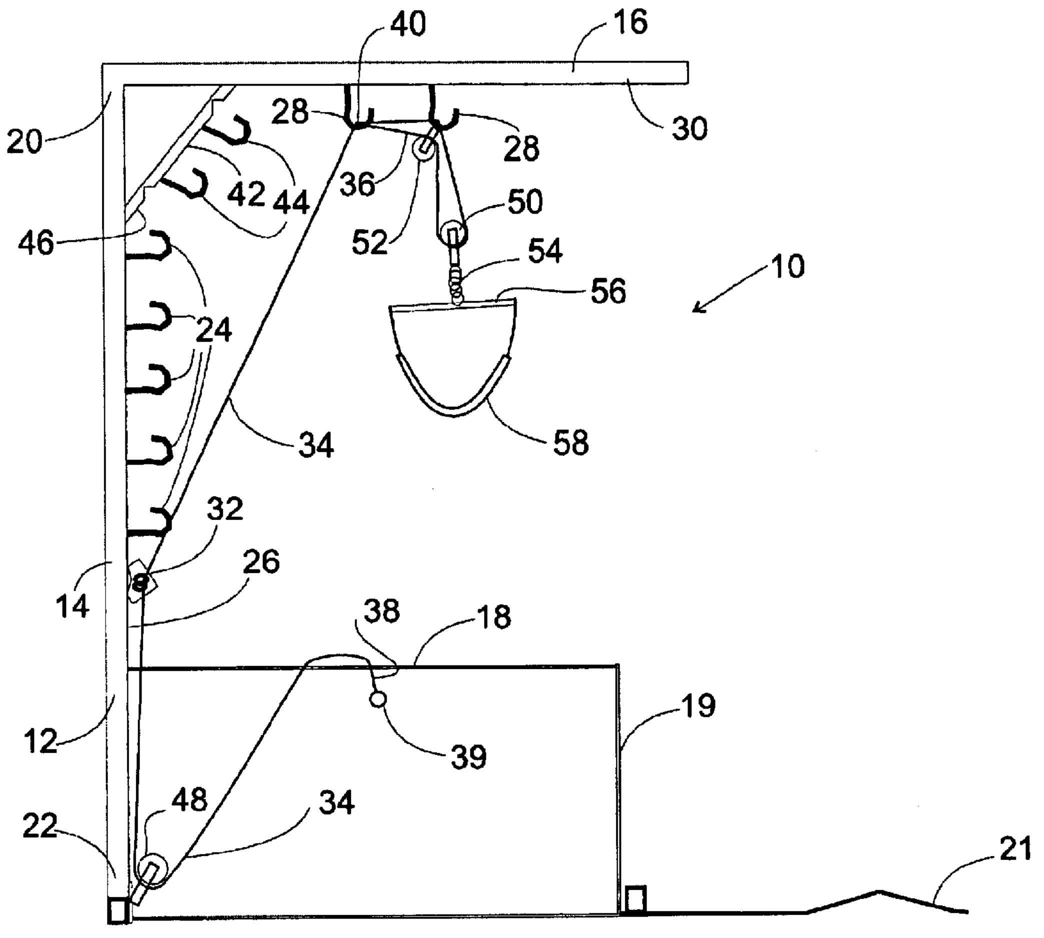
FIG. 1 is a front view of the traction force applying apparatus in accordance with the present invention.
Figure 2:
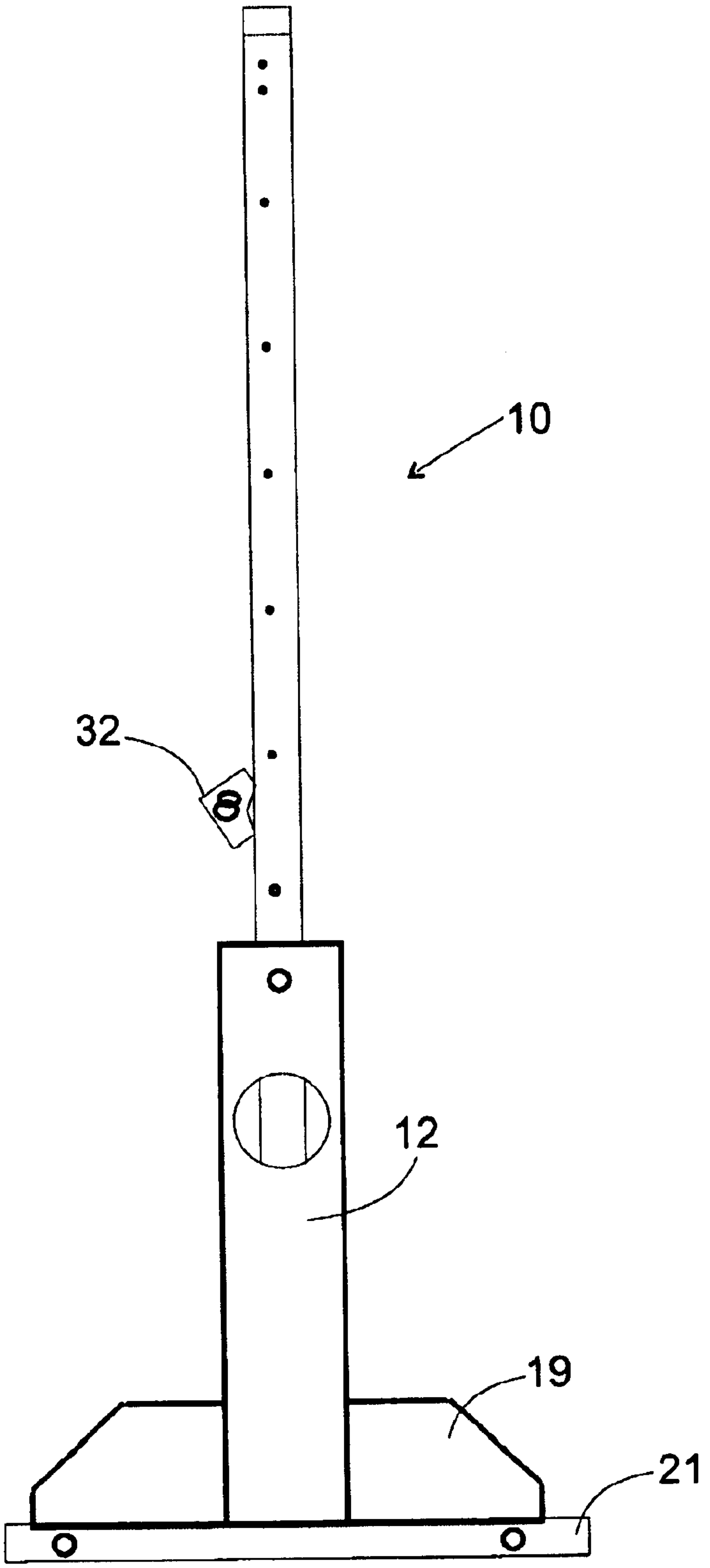
FIG. 2 is a left side view of the traction force applying apparatus shown in FIG. 1.

Referring now to FIGS. 1 and 2, a traction force applying apparatus 10 in accordance with the present invention is illustrated. The apparatus includes a frame 12 that has a first support bar 14, a second support bar 16 and a third support bar 18. The second support bar 16 is fixedly connected to the first support bar 14 at a first end 20 of the first support bar 14. The third support bar 18 is illustrated as being fixedly connected to first support bar 14 adjacent to but spaced from a second end 22 of the first support bar 14 (i.e., near the second end 22 of the first support bar). Alternatively, as will be shown, for example, in FIGS. 6–8, the third support bar can be connected at the second end of the first support bar at the base of the apparatus. In addition, a brace 42 is placed between the juncture of first bar 14 and second bar 16. Brace 42 preferably extends at a 45° angle with respect to both first bar 14 and second bar 16. Third support bar 18 is supported by a fourth bar 19. Extending from the base of bar 19 is a foot 21 that is sized to fit under the traction table shown in FIGS. 3–5.

A first set of plurality of hooks 24 are fixedly attached to a first side 26 of the first support bar 14. A second set of plurality of hooks 28 are fixedly attached to a first side 30 of second support bar 16. A third set of hooks 44 are fixedly attached to a first side 46 of brace 42 to increase the flexibility to the operator when positioning the rope 34. A one-way tensioning cleat 32 is fixedly connected to first support bar 14. Tensioning cleat 32, as can be seen in FIG. 2, projects at an angle of approximately 45° with respect to the direction of projection of the first set of plurality of hooks 24.

Figure 4:
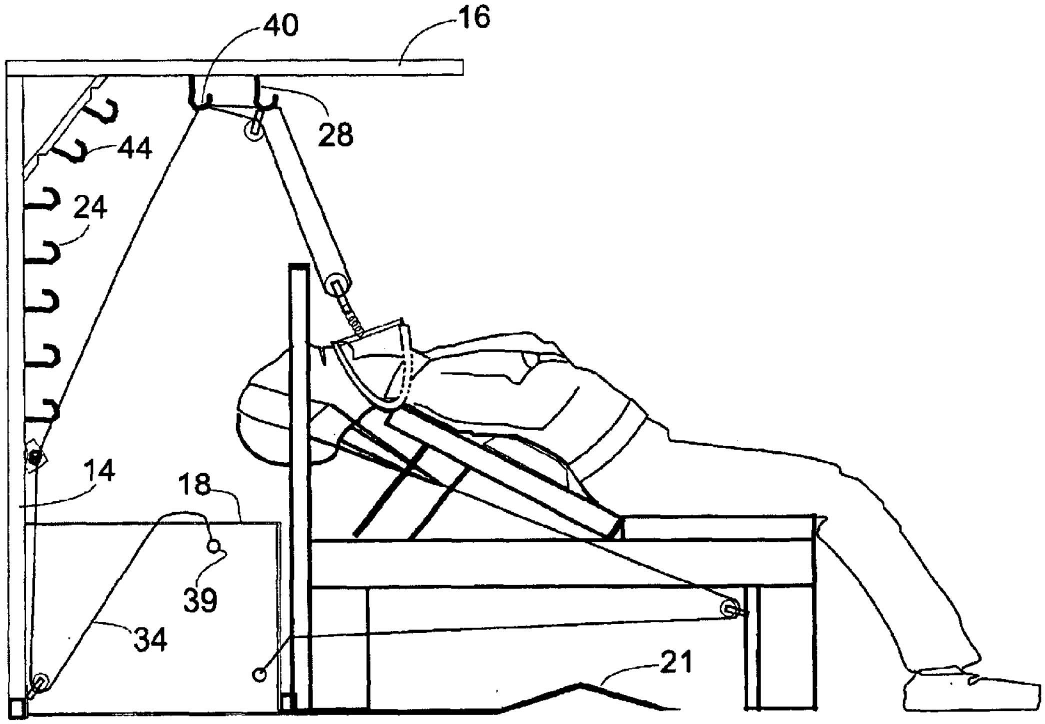
FIG. 4 is a front view of the traction force applying apparatus being used to support the neck of a patient who is receive treatment on the traction table.
Figure 5:
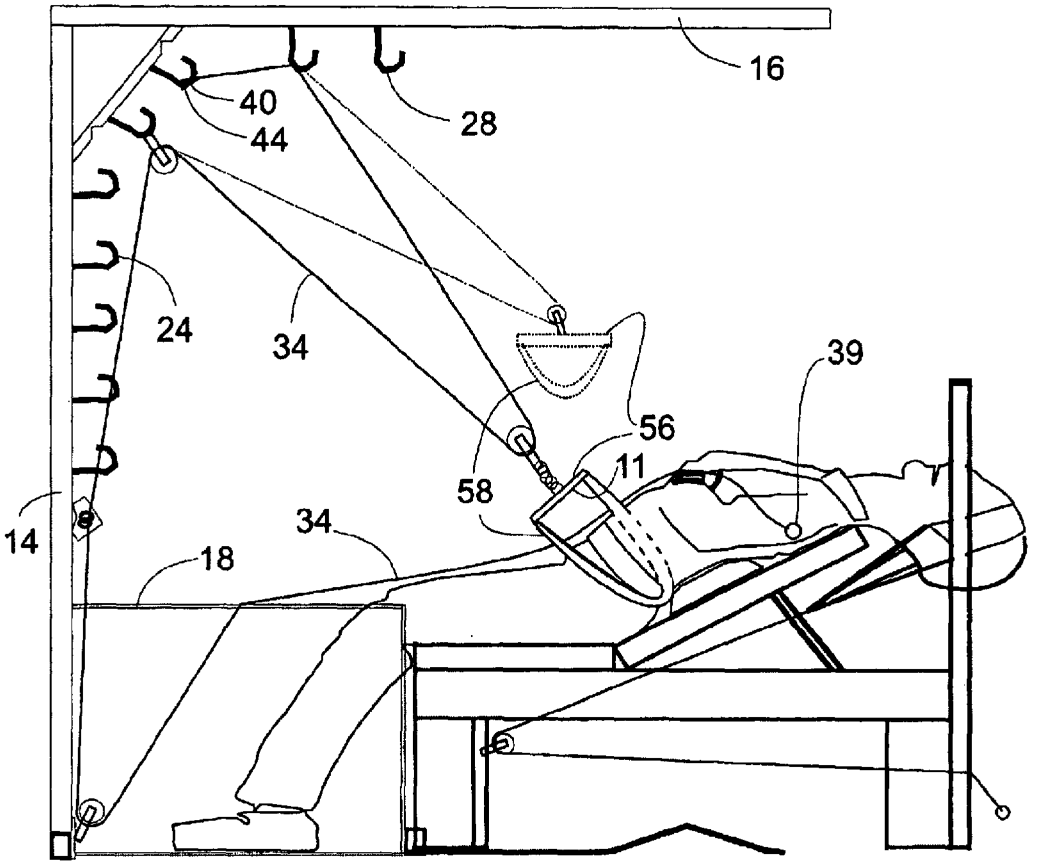
FIG. 5 is a front view of the traction force applying apparatus in a position to support the lumbar portion of the spine of a patient who is receiving treatment on the traction table.

A rope 34 has a first end 36 and a second end 38. First end 36 of rope 34 is fixedly attached to a loop 40 so that the first end 36 of rope 34 can be connected to any one of the hooks 24, 28, 44. Rope 34 can also be guided, as determined by the operator (e.g., a chiropractor), over any desired hooks 24, 28, 44 and through the tensioning cleat 32. Rope 34 is also preferably wrapped at least once around a series of pulleys 48, 50, 52 to increase the operator's leverage so that the operator does not have to use as much of his or her own work to provide the desired support to the patient. In other words, the rope is preferably wrapped around each of the pulleys at least once to increase the leverage for the operator. If each pulley has a 2:1 pull ratio, this allows the operator to apply only half the force on the rope end that needs to be applied to the patient. Adjacent to second end 38 of rope 34, pulley 50 is connected to a first end of a coil spring 54. A second end of coil spring 54 is connected to a crossbar 56. A strap 58 has a first end thereof connected to a first end of crossbar 56 and a second end thereof connected to a second end of crossbar 56. Crossbar 56 and strap 58 are sized to receive and support the neck of a patient as illustrated in FIG. 4 or can be of a somewhat larger size to accommodate the torso of a typical human adult about the lumbar portion of the spine as illustrated in FIG. 5. Thus, crossbar 56 and strap 58 can be disconnected from coil spring 54 and replaced with a second larger combination of cross bar 56' and strap 58', as shown in FIG. 5.

Figure 3:
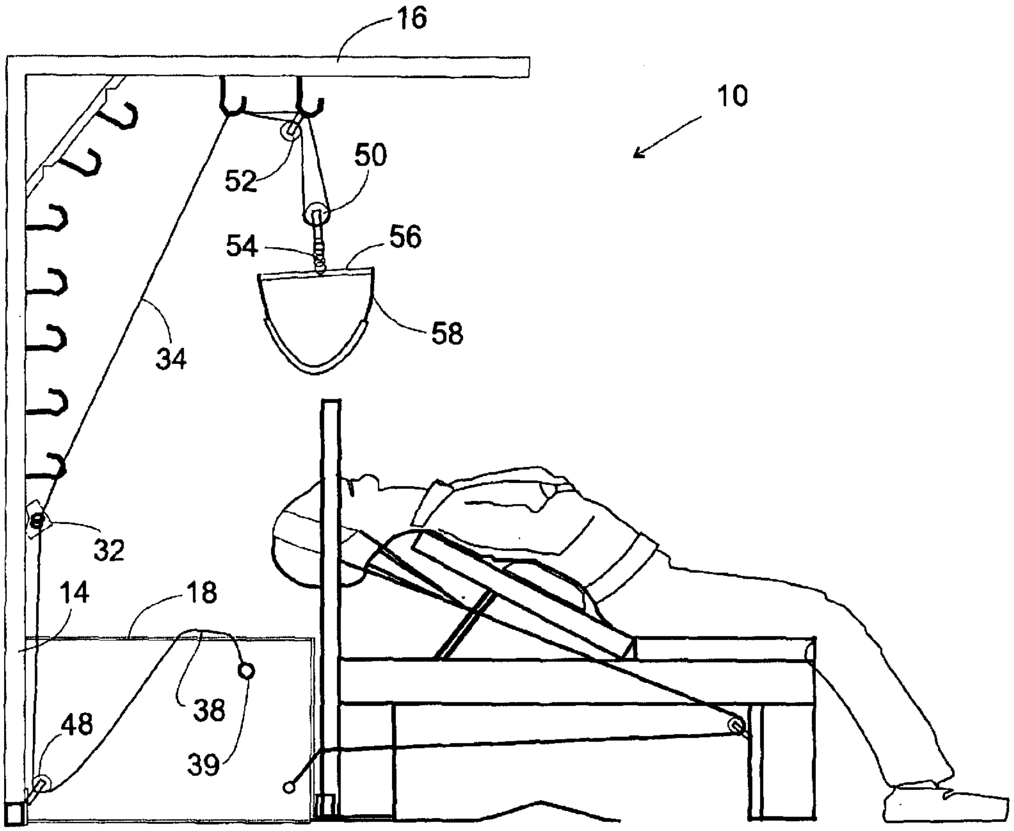
FIG. 3 is a front view of the traction force applying apparatus being used with a traction table.

Referring now to FIGS. 3–5, a method for directing a person's spine to an optimum position and/or shape with the use of the traction apparatus of the present invention is illustrated. The apparatus includes many hooks and pulleys so that the position of strap 58 can be adjusted to be placed in the proper position and angle below the neck, mid-back or lumbar to apply a force in the proper direction (e.g., posterior to anterior, horizontal, anterior to posterior or any variation thereof) as desired by the operator to restore the patient's spine to its natural biomechanical configuration. The operator can then pull on the rope, preferably from its second end to take full advantage of the leverage provided by the pulleys. By pulling on the rope a force is applied to the back of the neck, which force is a posterior to anterior force applied to the neck. When the desired force is reached, the operator can release the second end of the rope. But because the rope extends through the one-way cleat, the desired tension remains on the rope between the cleat and the rope's first end so that desired support for the neck can be achieved during the entire time period that the patient is receiving traction treatment on the traction table. The second end 38 of the rope is also preferably provided with a gripping device, such as, for example, a ball or ring 39 and is then preferably placed within easy reach of the patient so that, for whatever reason, the patient can release him or herself from the strap simply by pulling on the rope, which will cause the rope to open the cleat and release the tension in the rope.

Alternatively, as illustrated in FIG. 5 the device can be positioned with respect to a traction table to apply a lifting force to the back of the lumbar portion of the spine. A strap 58', and crossbar 56' are illustrated in FIG. 5 in the desired position to apply a lifting force to the back of the lumbar portion of the spine to apply a posterior to anterior force thereto.

Figure 6:
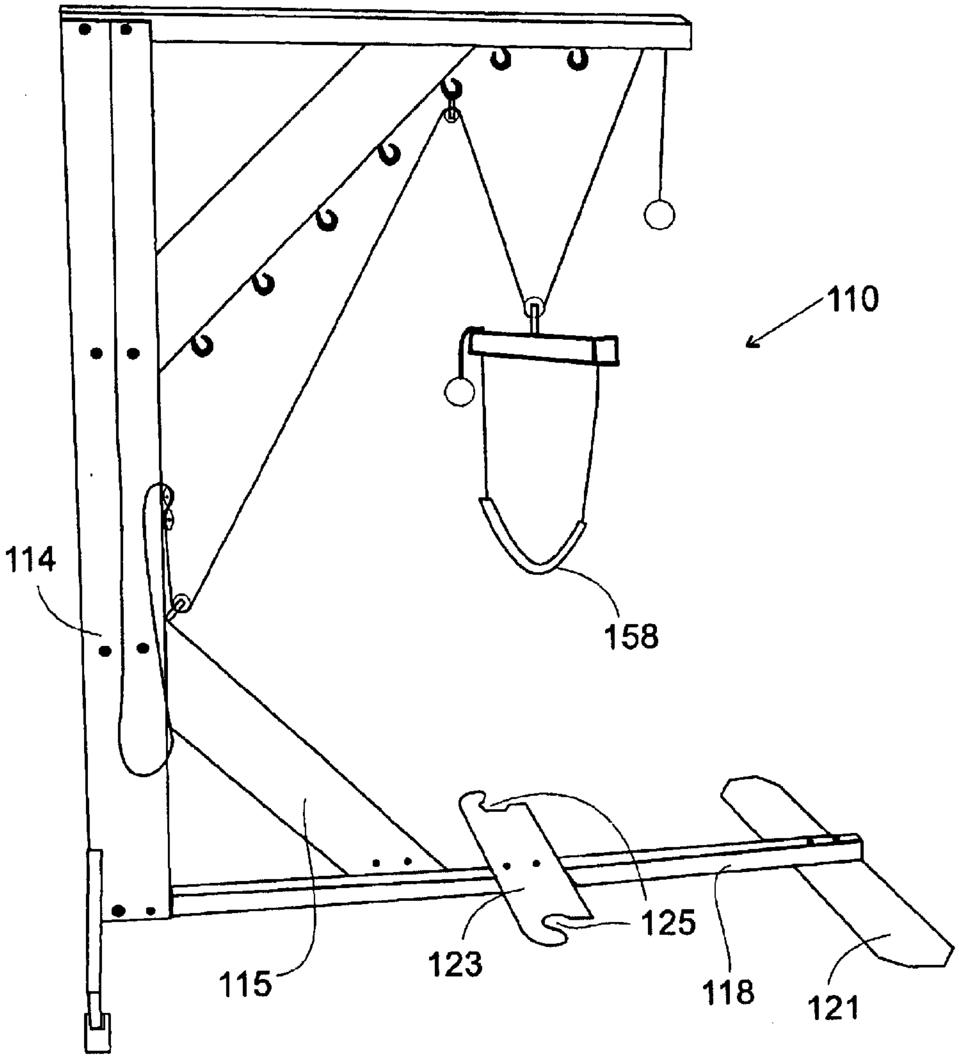
FIG. 6 is a perspective view of the traction force applying apparatus in accordance with a second embodiment of the present invention.
Figure 7:
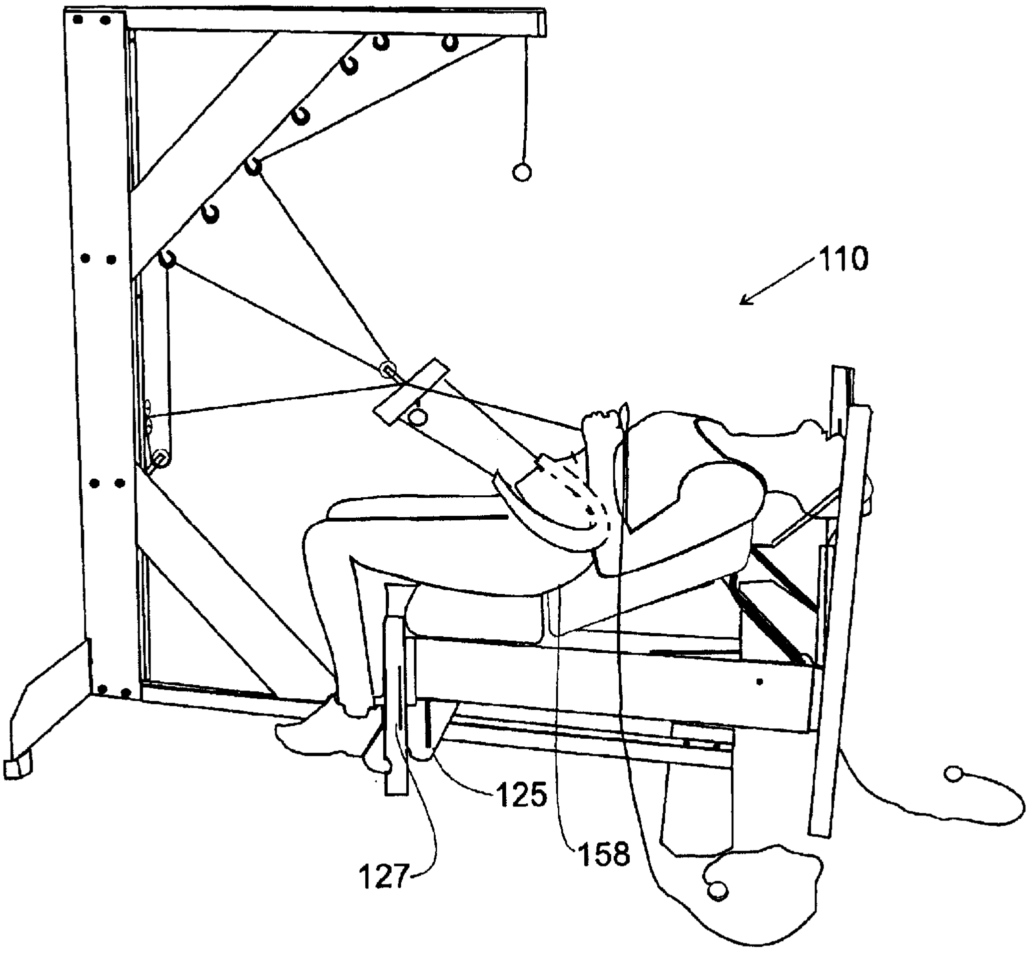
FIG. 7 is a perspective view of the traction force applying apparatus shown in FIG. 6 with a patient having force applied to the lumbar portion of the spine.
Figure 8:
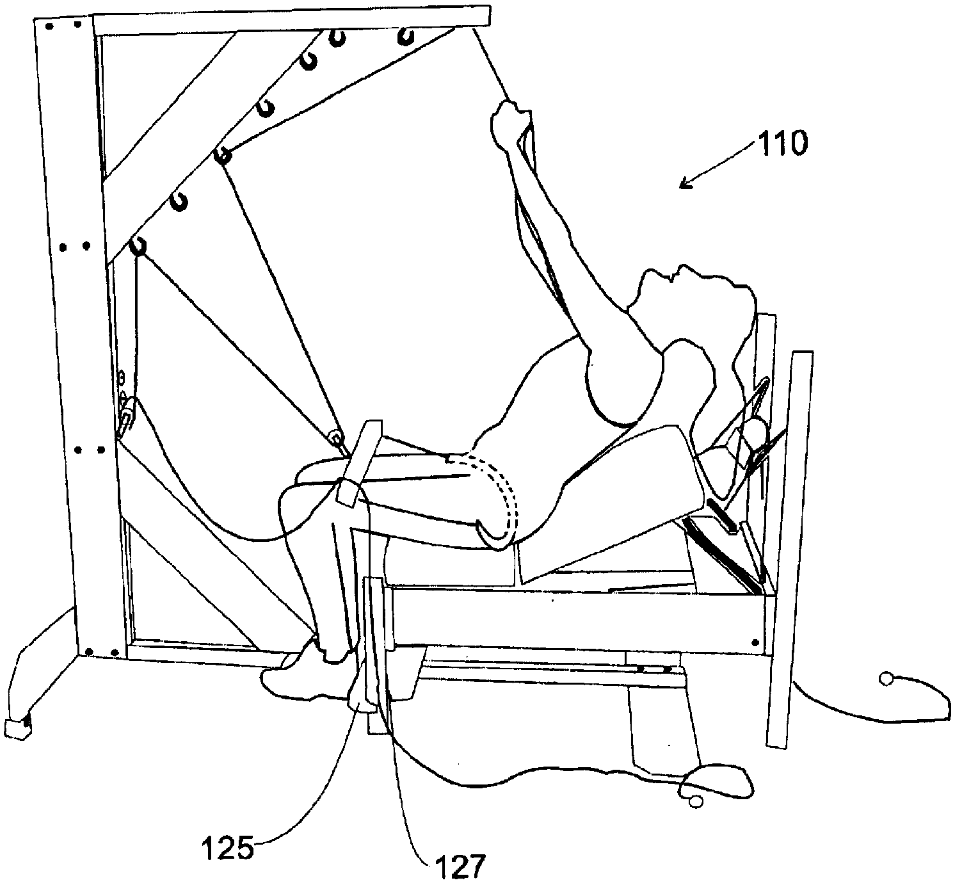
FIG. 8 is a perspective view of the traction force applying apparatus of FIG. 6 with a patient pulling herself out of the device.

Referring now to FIGS. 6–8, a modified second embodiment of the traction apparatus 110, in accordance with the present invention, is illustrated. This embodiment is similar to the first embodiment and is designed to be used as a module with a traction table, or maybe used alone, or maybe used in conjunction with other devices. Apparatus 110 includes a lower third bar 118 that is connected to first bar 114. A brace 115 is placed between a juncture of the first bar 114 and third bar 118 to reinforce this connection. In addition, a foot 121 is placed at a distal end of third bar 118 remote from the end where bar 118 is connected to first support bar 114. In addition, a positioning bar 123 is fixedly connected to third bar 118 so that, when apparatus 110 is used with a traction table, a pair of guide slots 125 (e.g., semi-circular in shape) may receive two of the legs of the traction table.

In this apparatus, the use of coil spring 54 has been eliminated to provide direct force to the portion of the body contacting strap 158.

Figure 9:
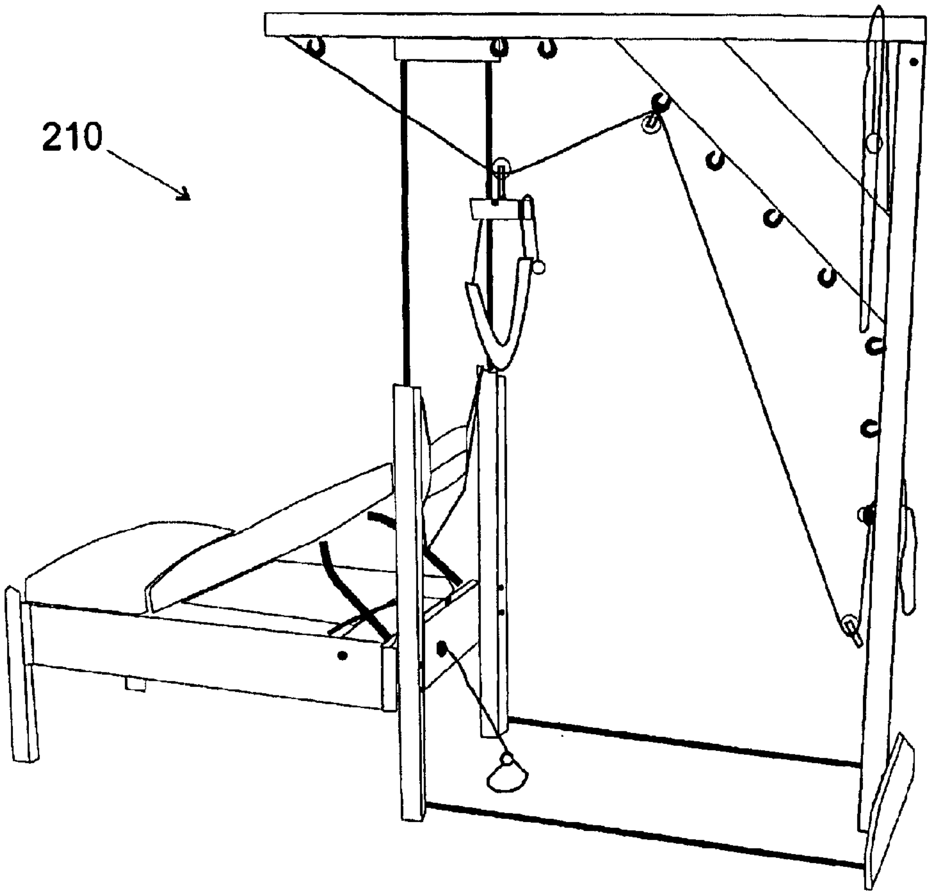
FIG. 9 is a perspective view of yet another traction force applying apparatus embodiment in accordance with the present invention.
Figure 10:
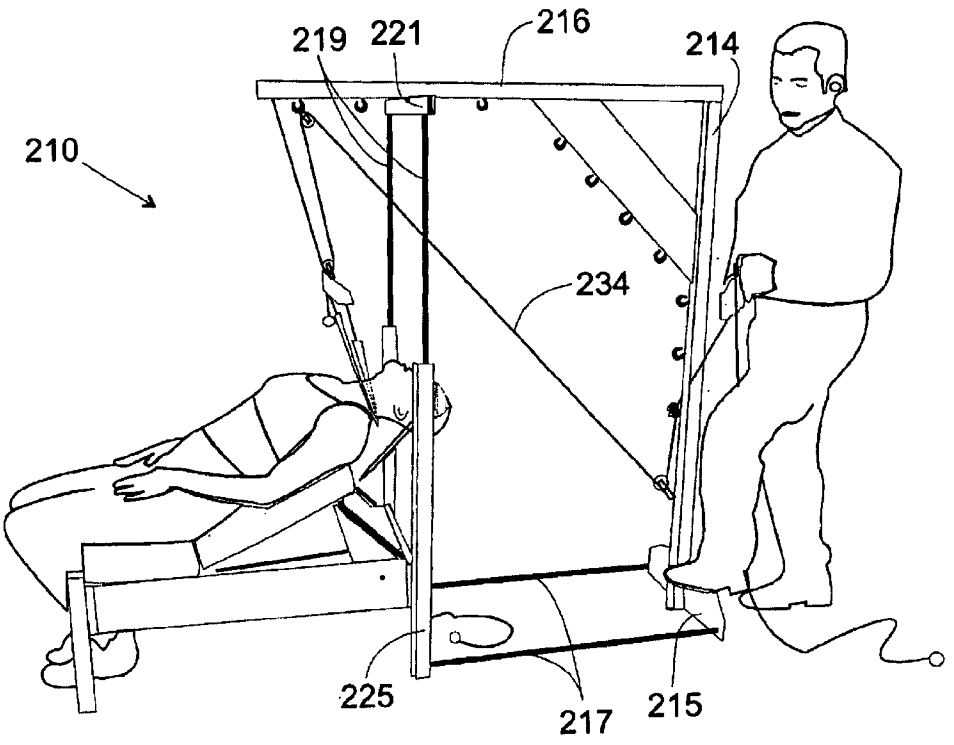
FIG. 10 is a perspective view of the traction force applying apparatus of FIG. 9 with a patient shown having force applied to the cervical portion of the spine.

Referring now to FIGS. 7 and 8, apparatus 110 is illustrated being used in conjunction with a traction table. As illustrated, the semi-circular recesses 125 receive two of the legs 127 of the traction table. Strap 158 has been positioned by an operator at a desired position to apply force to the lumbar portion of the spine. FIG. 8 illustrates how a patient can use the free end of the rope to lift herself from the table. Of course, if desired, the apparatus 110 can be provided with a second rope and a second cleat, preferably positioned at a 90° angle with respect to the first cleat so that a second strap can be used to apply force to a second portion of the body. Referring now to FIGS. 9 and 10, another embodiment 210 of the apparatus in accordance with the present invention is illustrated. This apparatus differs from the first in that it is made as one unit with a traction table. Instead of a third bar being connected at the second end of the first support bar 214, a cross brace 215 is connected to the second end of first support bar 214. A pair of connecting rods 217 connect either end of cross bar 215 to separate legs 225 of the traction table. Additionally, the forward free end of first support bar 214 is illustrated being supported by a pair of vertically directed bars 219 extending upwardly from the top of legs 225. Bars 219 connect to a cross-brace 221 that is fixedly connected to second support bar 216.

FIG. 10 illustrates an operator pulling on the rope 234 to apply a desired force to the cervical portion of the spine of a patient to restore the patient's spine to its natural biomechanical configuration. As discussed above, once the desired force is achieved, the first end of the rope 38 is placed near the patient so that she may pull on the rope to remove the tension in the rope, thereby removing the force being applied to the cervical portion of the spine.

Figure 11:
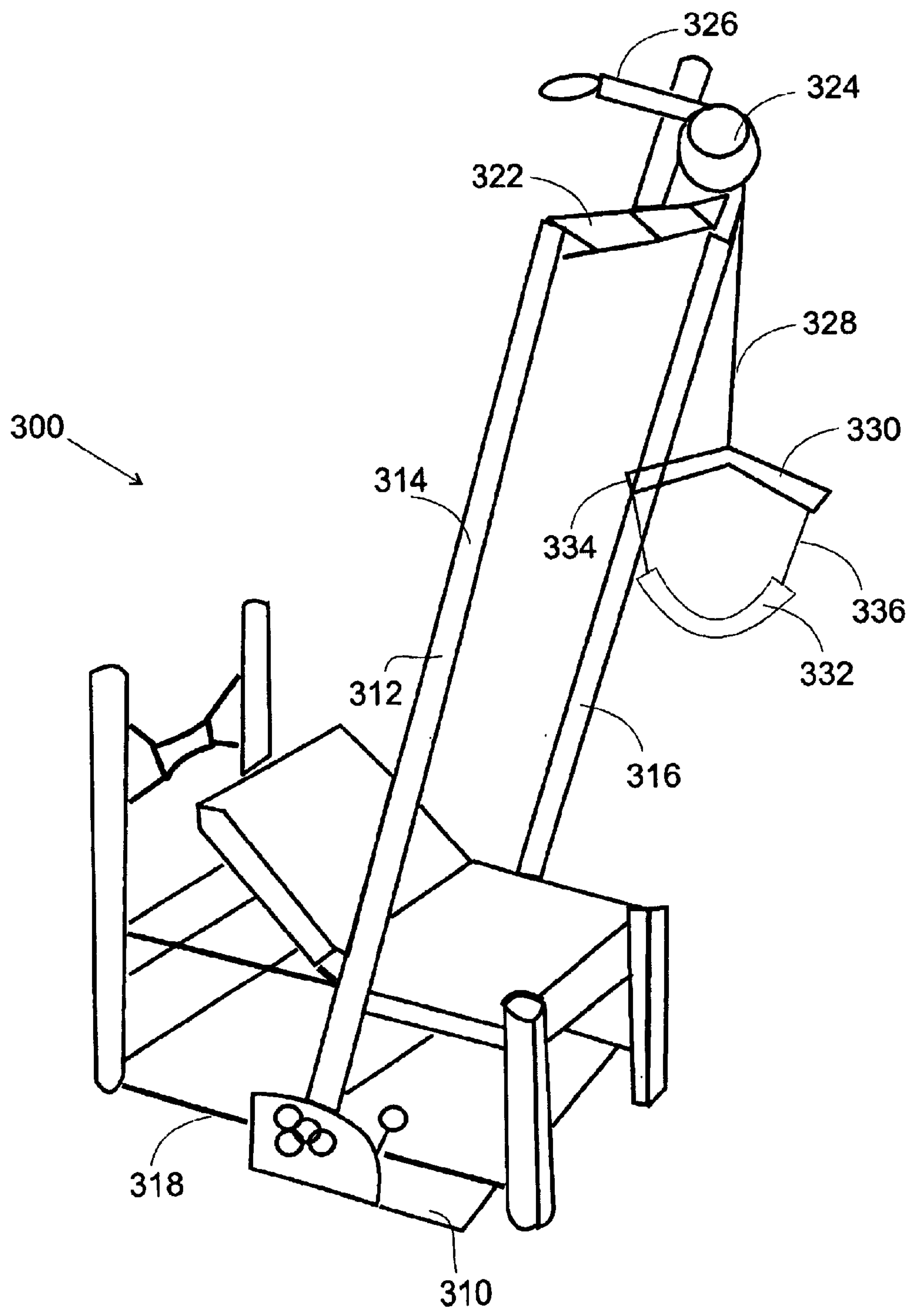
FIG. 11 is a perspective view of the traction force applying apparatus in accordance with a third embodiment of the present invention.
Figure 12:
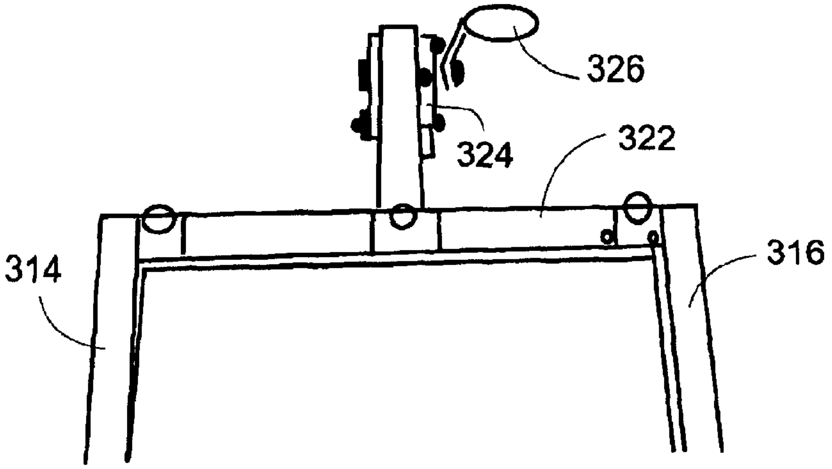
FIG. 12 is a partial plan view of an upper portion of a U-shaped frame.
Figure 13:
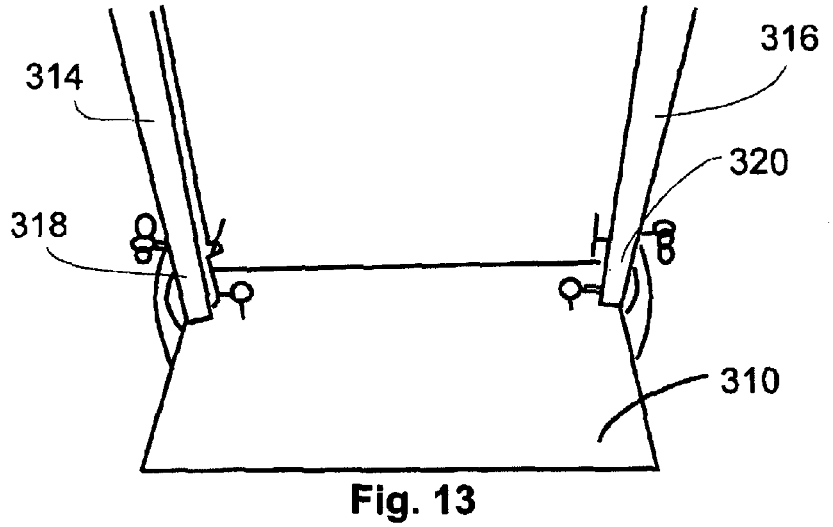
FIG. 13 is a partial plan view of a lower portion of the U-shaped frame and the base.
Figure 14:
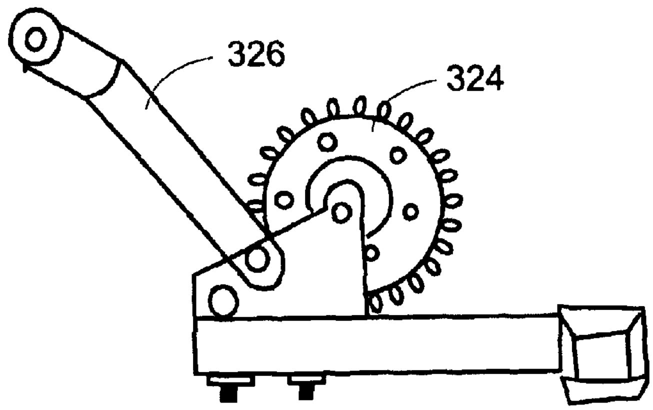
FIG. 14 is a side view of the winch.

Referring now to FIGS. 11–16, a third embodiment of the traction force applying apparatus 300, in accordance with the present invention, is illustrated. This embodiment of the traction force applying apparatus 300 includes a base 310 and a U-shaped frame 312 connected to the base. U-shaped frame 312 has a pair of legs 314, 316. As illustrated in FIGS. 11 and 13, a distal end 318, 320 of each of the legs 314, 316 is selectively pivotably connected to base 310 such that it can be selectively fixedly connected to base 310 at various angles with respect to the base.

U-shaped frame 312 also includes a cross bar 322 to connect the other ends of legs 314, 316 to each other. Winch 324 is fixedly connected to cross bar 322. Winch 324 is of conventional structure and includes a crank arm 326 to raise and lower a rope 328. Of course, rope 328 could be a chain, kit, cable, wire or any other type of line that may be utilized by winch 324. The distal end of rope 328 is connected to a second cross bar 330. A strap 332 has a first end 334 and a second end 336. A first end 334 of strap 332 is connected to a first end of second cross bar 330. Second end 336 of strap 332 is connected to a second end of second cross bar 330.

Figure 15:
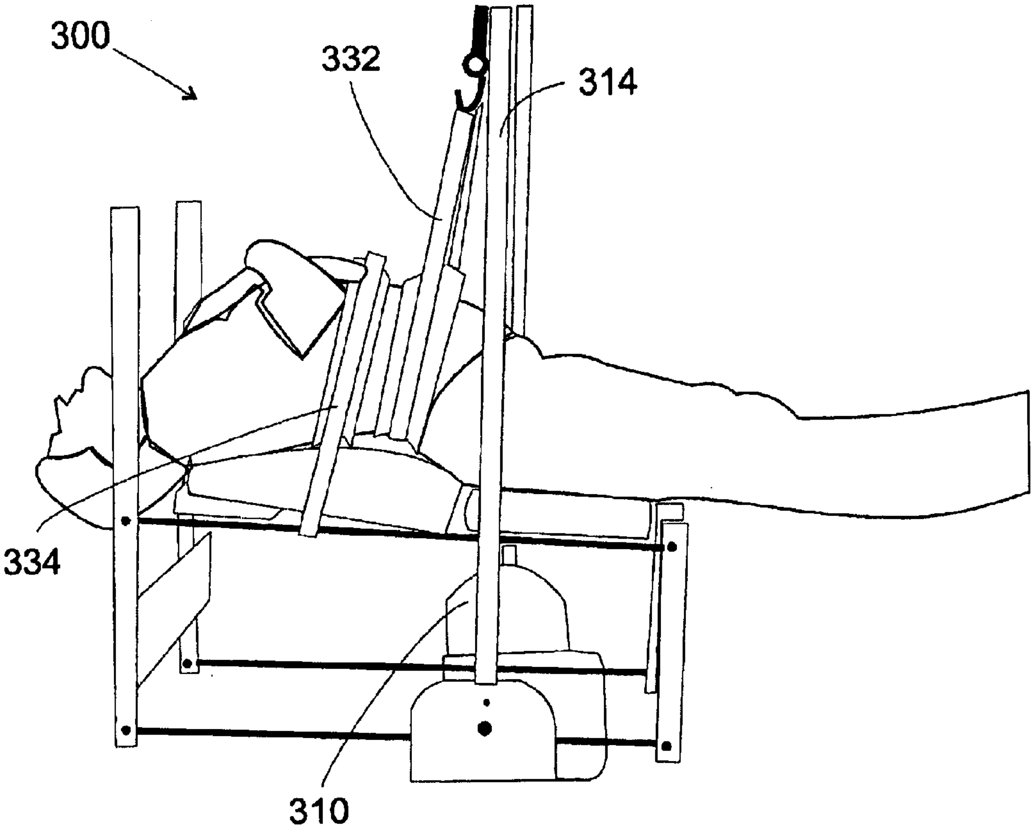
FIG. 15 is a side view of the traction force applying apparatus of FIG. 11 with a patient shown having a force applied to the lumbar portion of the spine.
Figure 16:
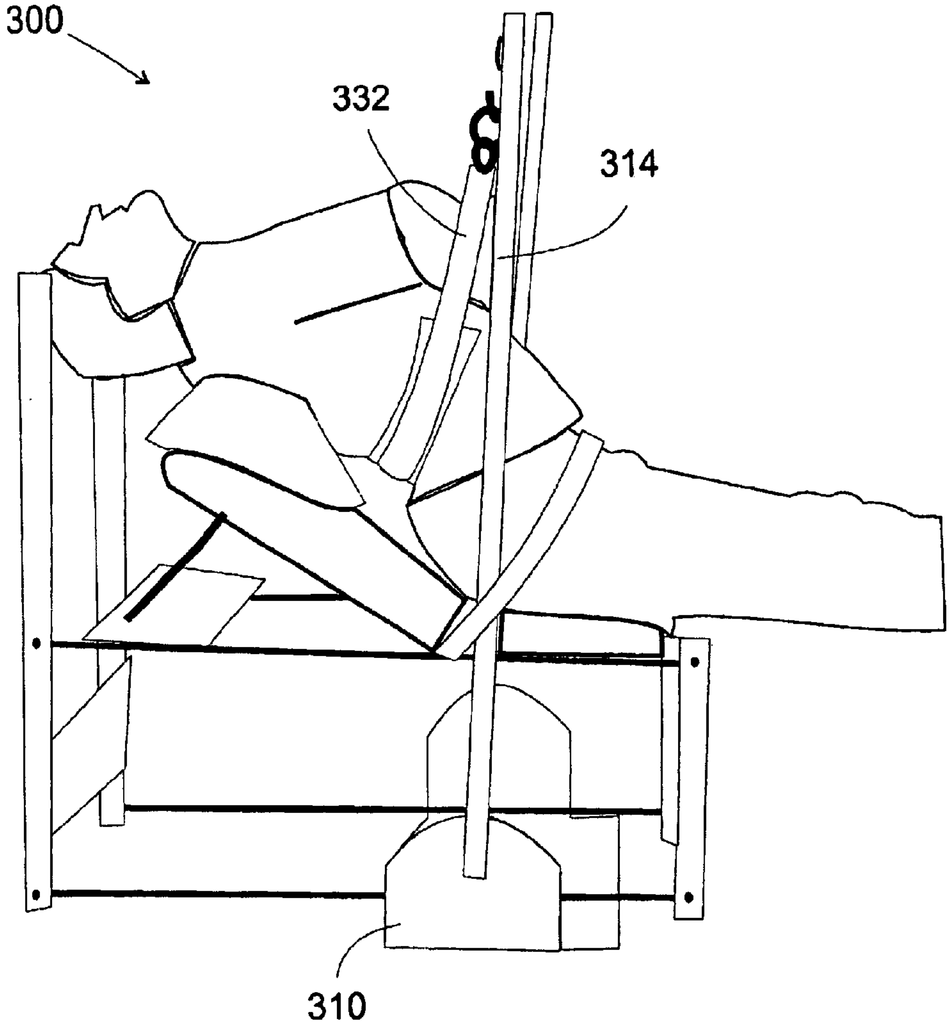
FIG. 16 is a side view of the traction force applying apparatus of FIG. 11 with a patient shown having a force applied to the thoracic portion of the spine.

As illustrated in FIGS. 11, 15 and 16, the traction force applying apparatus 300 may be utilized with a traction table, which is capable of restoring a patients spine to its natural biomechanical configuration. As illustrated in FIGS. 11, 15 and 16, the traction table is disposed above base 310 and between legs 314, 316 of the traction force applying apparatus 300. As illustrated in FIG. 15, a second strap 334, which is attached to the traction table may be used to hold a patient down on the traction table to allow strap 332 to apply a force to the body in a direction counter to the direction that the force is applied by the second strap 334. Thus, strap 332 can then apply a greater force that was previously limited by the weight of the patient. The second strap thus acts as an anchor for the body. Strap 334 is preferably placed about the chest or stomach, but may be placed about the thighs or pelvis.

Figure 17:
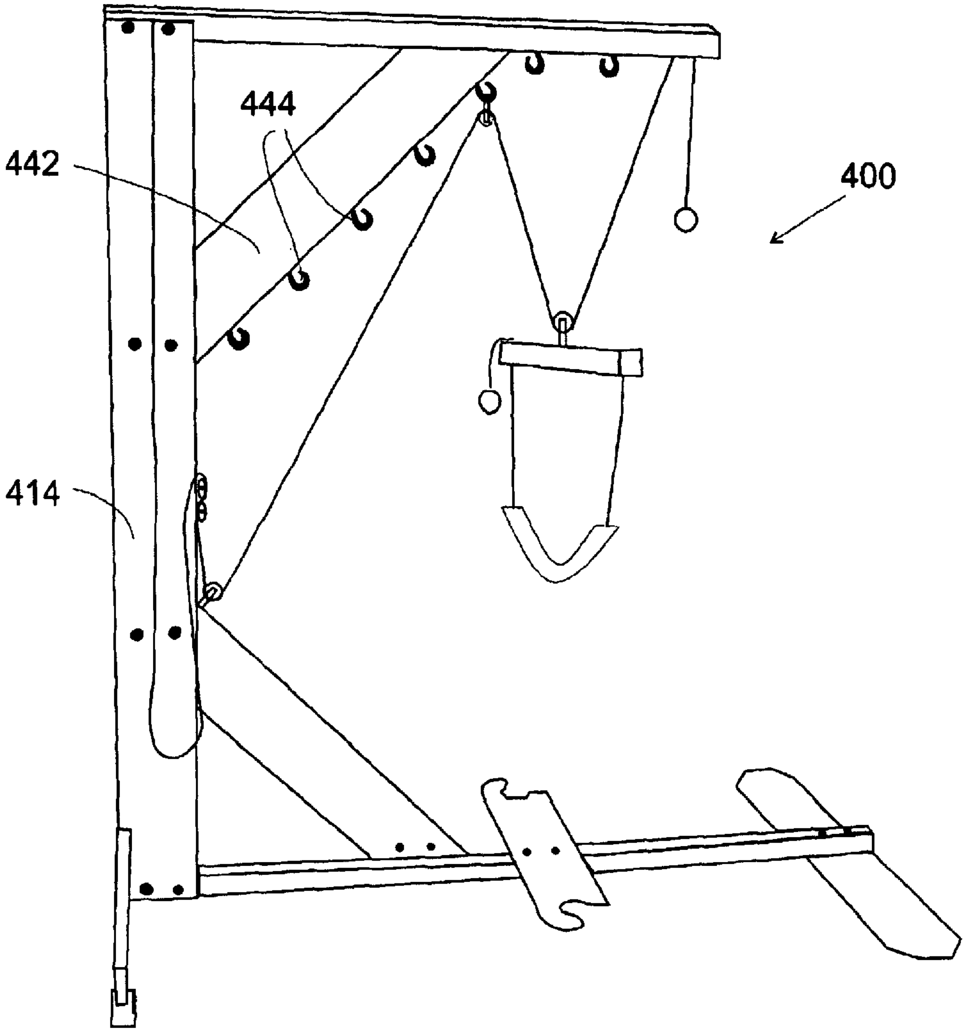
FIG. 17 is a perspective view of yet another traction force applying apparatus embodiment in accordance with the present invention.
Figure 18:
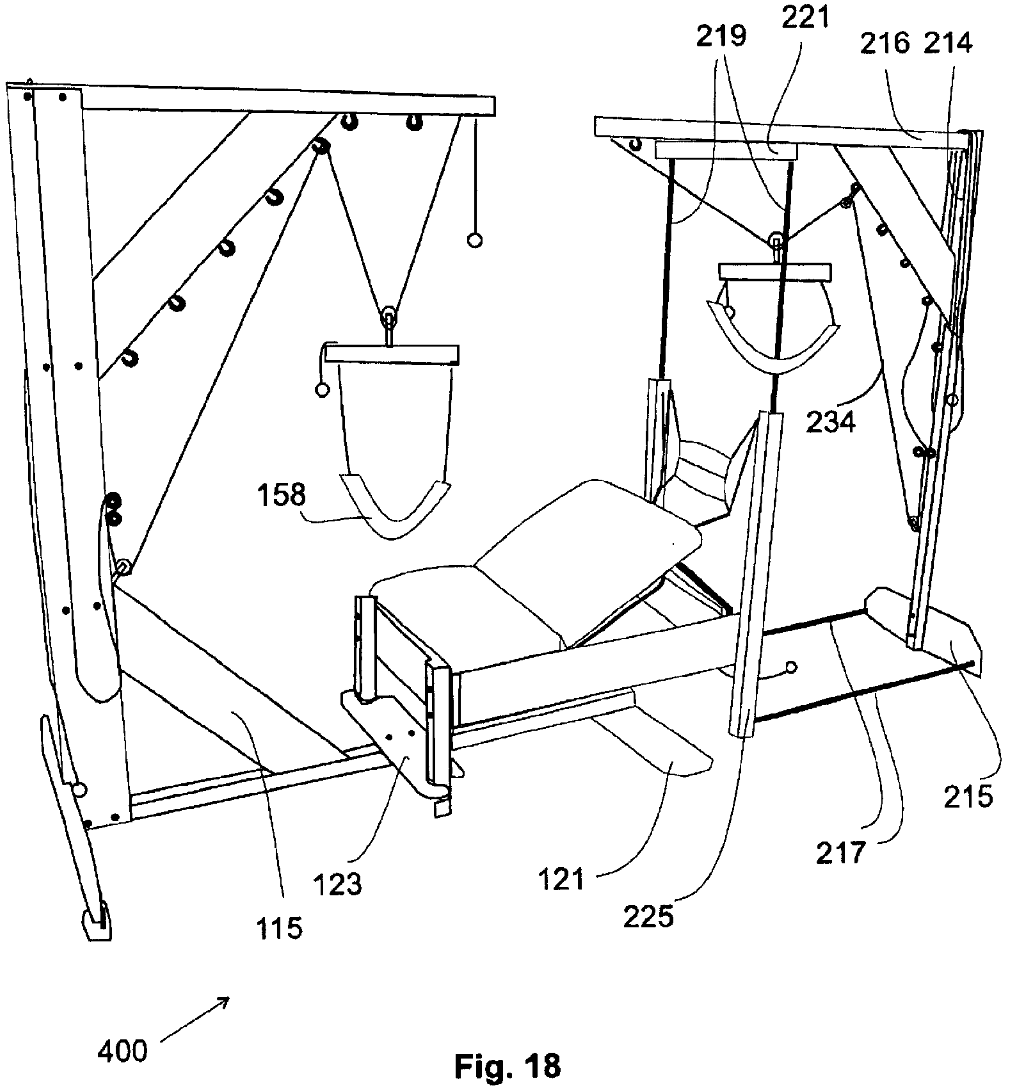
FIG. 18 is a perspective view of the traction force applying apparatus of FIG. 17, the apparatus of FIG. 9 and a traction table.

Referring now to FIGS. 17 and 18, another embodiment 400 of the apparatus in accordance with the present invention is illustrated. This embodiment differs from the first in that it is made with a plurality of hooks 444 on the brace 442, and none on the first bar 414. As illustrated in FIG. 18, this embodiment may be used in conjunction with the embodiment shown in FIGS. 9 and 10. Of course, one skilled in the art would readily recognize that other embodiments of the present inventions may be used together, in a manner similar to as illustrated in FIG. 18. For example, the first embodiment and the embodiment of FIGS. 9 and 10 can be used together.

Alternatively, the traction force applying apparatus may be used without a traction table. Of course, any of the traction force applying apparatus embodiments disclosed in the present invention may be used with or without a traction table. In addition, any of the disclosed embodiments of the traction force applying apparatus can be used with the patient standing or lying down.

Having described the presently preferred exemplary embodiment of a traction force applying apparatus and method of using the same in accordance with the present invention, it is believed that other modifications, variations and changes will be suggested to those skilled in the art in view of the teachings set forth herein. For example, the straps can be positioned to apply a downward (i.e., anterior to posterior) force to the hips or shoulders to cause a posterior to anterior force to be applied to the spine. It is, therefore, to be understood that all such modifications, variations, and changes are believed to fall within the scope of the present invention as defined by the appended claims.

What is claimed is:

1. A traction force applying apparatus for use with a traction table, said traction table having a set of front legs and a set of hind legs, said apparatus comprising, a self-supporting frame having:

a first support bar, said first support bar having a top end and a bottom end, said first support bar having a longitudinal axis that is aligned vertically;

a second support bar having a first end and a second end, said first end being connected to said top end of said first support bar, said second support bar having a longitudinal axis that is aligned horizontally;

a base for supporting the frame including, a third support bar having a first end, and a second end said first end of said third support bar being connected to said bottom end of said first support bar, said third support bar having a longitudinal axis that is aligned horizontally;

a brace mounted between said first support bar and said second support bar;

a first set of plurality of hooks being fixedly attached to a first side of one of said first support bar and said second support bar;

a one-way tensioning cleat being fixedly connected to said first support bar;

a rope having a first end and a second end, said first end of said rope being selectively connectable to one of said plurality of hooks in said first set, said rope extending through said cleat to place a desired tension on said rope between said cleat and said first end of said rope; and a positioning bar with guide slots connected to said second end of said third support bar for receiving and positioning the apparatus with the legs of the traction table so that the traction table is positioned in one of a plurality of positions with respect to the apparatus, wherein in one of the positions the set of front legs are in contact with the apparatus and the set of hind legs are spaced from the apparatus, and in another one of the positions the set of hind legs are in contact with the apparatus and the set of front legs are spaced from the apparatus.

2. The traction force applying apparatus according to claim 1, further comprising a pulley connected to the first support bar, said rope having a second end that is guided over the pulley to a position adjacent to said third bar.

3. The traction force applying apparatus according to claim 1, further comprising a plurality of pulleys connected to the first support bar, wherein said rope is guided over the plurality of pulleys.

4. The traction force applying apparatus according to claim 1, wherein said rope is guided around at least one hook of said first set of plurality of hooks and at least one hook of a second set of plurality of hooks.

5. The traction force applying apparatus according to claim 1, further comprising a pulley connected to the second bar, said rope, adjacent to said rope first end, being wrapped around said pulley.

6. The traction force applying apparatus according to claim 5, further comprising a compression spring being connected, at a first end thereof, to said pulley.

7. The traction force applying apparatus according to claim 6, further comprising a strap being connected to a second end of said spring.

8. The traction force applying apparatus according to claim 7, further comprising a cross bar being directly connected to said second end of said spring, said strap having a first end connected to a first end of said cross bar, and said strap having a second end connected to a second end of said cross bar.

9. The traction force applying apparatus according to claim 1, wherein said frame include a brace mounted between said first bar and said second bar, at least one hook being fixedly attached to a first side of said brace.

10. The traction force applying apparatus according to claim 1, wherein said tensioning cleat is disposed at an angle of approximately 45° with respect to a direction of projection of said first set of plurality of hooks.

11. The traction force applying apparatus according to claim 1, wherein said second bar is connected to said first bar at approximately a 90° angle.

12. The traction force applying apparatus according to claim 11, wherein said third bar is connected to said first bar at approximately a 90° angle.

13. The traction force applying apparatus according to claim 1, wherein said second end of said rope is fixedly attached to a grip.

14. A traction force applying apparatus with a traction table having a set of front legs and a set of hind legs comprising, a self-supporting frame having:

a first support bar, said first support bar having a top end and a bottom end, said first support bar having a longitudinal axis that is aligned vertically;

a second support bar having a first end and a second end, said first end being connected to said top end of said first support bar, said second support bar having a longitudinal axis that is aligned horizontally;

a base for supporting the frame including, a third support bar having a first end and a second end, said first end of said third support bar being connected to said bottom end of said first support bar, said third support bar having a longitudinal axis that is aligned horizontally;

a brace mounted between said first support bar and said second support bar;

a first set of plurality of hooks being fixedly attached to a first side of said brace;

a second set of plurality of hooks being fixedly attached to a first side of said second support bar;

a one-way tensioning cleat being fixedly connected to said first support bar;

a rope having a first end and a second end, said first end of said rope being selectively connectable to one of said plurality of hooks in said first set and said second set, said rope extending through said cleat to place a desired tension on said rope between said cleat and said first end of said rope; and a positioning bar with guide slots for receiving and positioning the apparatus with the legs of the traction table so that the traction table is positioned in one of a plurality of positions with respect to the apparatus, wherein in one of the positions the set of front legs are in contact with the apparatus and the set of hind legs are spaced from the apparatus, and in another one of the positions the set of hind legs are in contact with the apparatus and the set of front legs are spaced from the apparatus.

15. The traction force applying apparatus according to claim 14, further comprising a pulley connected to the first support bar, said rope has a second end that is guided over the pulley to a position adjacent to said third bar.

16. The traction force applying apparatus according to claim 14, further comprising a plurality of pulleys connected to the first support bar, said rope is guided over the plurality of pulleys.

17. The traction apparatus according to claim 16, wherein said rope is guided around at least one hook of said first set of plurality of hooks and at least one hook of said second set of plurality of hooks.

18. The traction force applying apparatus according to claim 14, further comprising a pulley connected to the second bar, said rope, adjacent to said rope first end, being wrapped around said pulley.

19. The traction force applying apparatus according to claim 18, further comprising a compression spring being connected, at a first end thereof, to said pulley.

20. The traction force applying apparatus according to claim 19, further comprising a strap being connected to a second end of said spring.

21. The traction force applying apparatus according to claim 20, further comprising a cross bar being directly connected to said second end of said spring, said strap having a first end connected to a first end of said cross bar, and said strap having a second end connected to a second end of said cross bar.

22. The traction force applying apparatus according to claim 14, wherein said tensioning cleat is disposed at an angle of approximately 45° with respect to a direction of projection of said first set of plurality of hooks.

23. The traction force applying apparatus according to claim 14, wherein said second bar is connected to said first bar at approximately a 90° angle.

24. The traction force applying apparatus according to claim 23, wherein said brace is connected to said first bar and said second bar at approximately a 45° angle.

25. The traction force applying apparatus according to claim 14, wherein said second end of said rope is fixedly attached to a grip.

* * * * *